United States Patent [19]
Henriksen

[11] Patent Number: 6,136,859
[45] Date of Patent: Oct. 24, 2000

[54] PHARMACEUTICAL FORMULATION FOR TREATING LIVER DISORDERS

[75] Inventor: Bent Henriksen, Morpeth, Denmark

[73] Assignee: Pharma Nord ApS, Vojens, Denmark

[21] Appl. No.: 09/177,555

[22] Filed: Oct. 23, 1998

[30] Foreign Application Priority Data

Oct. 24, 1997 [GB] United Kingdom ............... 9722361

[51] Int. Cl.$^7$ .................. A61K 31/355; A61K 31/375; A23L 1/30
[52] U.S. Cl. ............................................ 514/561
[58] Field of Search ................... 514/438, 474, 514/706, 904, 905, 838, 183, 185, 247, 762, 766, 715, 723, 359, 385, 393, 492, 675, 690, 449, 451, 454, 557, 561, 562, 569, 579, 725, 740, 742, 763, 893, 894; 424/702, 941; 426/72, 74

[56] References Cited

U.S. PATENT DOCUMENTS

| | | | |
|---|---|---|---|
| 4,784,852 | 11/1988 | Johansson | 424/702 |
| 5,895,652 | 4/1999 | Giampapa | 424/195.1 |

FOREIGN PATENT DOCUMENTS

| | | |
|---|---|---|
| 0 519 876 | 12/1992 | European Pat. Off. . |
| 196 53 100 A1 | 7/1998 | Germany . |
| WO 96/17584 | 6/1996 | WIPO . |
| WO 97/25864 | 7/1997 | WIPO . |
| WO 98/33494 | 8/1998 | WIPO . |

OTHER PUBLICATIONS

Knudsen et al., 'Multiple antioxidants protect against heme protein and lipid oxidation in kidney tissue' (1996), Free Radial Biology & Medicine, vol. 20, No. 2, pp. 165–173.

Chen et al., 'Protection by multiple antioxidants against lipid peroxidation in rat liver homogenate' (1996), Lipids, vol. 31, No. 1, pp. 47–50.

Chen et al., 'Protection of multiple antioxidants against heme protein oxidation and lipid peroxidation induced by CBrCl3 in liver, lung, kindey, heart, and spleen' (1996), Journal of Agriculture & Food Chemistry, vol. 44, No. 3, pp. 854–858.

Chen, H. & Tappel A.L., *Free Radical Biol. & Med.*, 16 (4), 437–444, (1994).

Chen, H. & Tappel A.L., *Free Radical Biol. & Med.*, 18(5), 949–953 (1995).

Chen, H. & Tappel A.L., *Free Radical Res.*, 22 (2), 177–186 (1995).

De Oliveira, J., *J Orthomolecular Med.*, 13 (3), 176–178 (1998).

*Primary Examiner*—John Pak
*Assistant Examiner*—Frank Choi
*Attorney, Agent, or Firm*—Oblon, Spivak, McCelland, Maier & Neustadt, P.C.

[57] ABSTRACT

A pharmaceutical formulation comprising organic or inorganic selenium, β-carotene or vitamin A, ascorbic acid or a salt or ester thereof; α-tocopherol or a derivative thereof, methionine and coenzyme Q10 together with a pharmaceutically acceptable carrier therefor suitable for treating such diseases as primary biliary cirrhosis.

8 Claims, No Drawings

PHARMACEUTICAL FORMULATION FOR TREATING LIVER DISORDERS

The present invention relates to a pharmaceutical formulation suitable for use in the treatment of liver disorders such as primary biliary cirrhosis (PBC), viral hepatitis, steatohepatitis, alcoholic cirrhosis and related hepatic and biliary disorders. The invention also relates to the use of particular vitamins, amino acids, trace elements and ubiquinone for the preparation of a medicament suitable for the treatment of such liver disorders.

Primary biliary cirrhosis is a chronic cholestatic liver disease with an autoimmune aetiology which results in the destruction of the bile ducts in the liver. The disease is progressive in nature, with a significant proportion of affected patients going on to develop cirrhosis with all its sequelae.

Females are more commonly affected, with approximately 90% of all cases of PBC occurring in females. This disease has been diagnosed in patients as young a 23 years and as old as 72. The majority of cases are diagnosed in the 40–60 age group.

Whilst patients suffering from PBC are at risk of developing cirrhosis, such patients are often profoundly symptomatic with significant impairment of their quality of life. The most common presenting symptom is pruritus or generalised itching. This may occur after the onset of birth control use or during pregnancy. Jaundice (yellowing of the eyes, skin and under the tongue) is seen as a later finding. More recently it has been appreciated that PBC patients can suffer from debilitating fatigue, indeed population surveys have suggested that fatigue may be the commonest symptom of PBC occurring in up to 80% of patients. The effects of PBC related fatigue on patient quality of life can be significant.

Other symptoms seen in PBC include bone and joint pains, abdominal pains and dry eyes and dry mouth from kerato-conjunctivitis sicca. Complications of PBC include portal hypertension, oesophageal varices, hepatic encephalopathy and osteomalacia.

Diagnosis is by routine blood tests, which reveal elevations in the blood cholesterol and alkaline phosphatase levels. Special serological tests (anti-mitochondrial antibodies) help confirm the diagnosis, with liver biopsy providing absolute confirmation.

Patients who are without symptoms at the time of diagnosis have a better prognosis and can live 10 years or more, often without symptoms. Those who manifest symptoms of this disease, in contrast, have only a 50% survival rate beyond 5 years.

Currently there is no specific treatment for primary biliary cirrhosis. Treatment largely consists of supportive care for cirrhosis and its complications. These patients benefit from treatment of high cholesterol and itching with such medications as cholestyramine. A diet that is low in fat is recommended. Alcoholic beverages must be avoided. Other medicaments, such as paracetomol, that are primarily metabolised by the liver, require dosage adjustment.

Many drug treatments have been tried in PBC with the principal aim of slowing the rate of progression of the disease to cirrhosis. Drugs that have been studied include D-penicillamine, azathioprine, chlorambucil, colchicine, cyclosporin-A and prednisolone, however, a combination of limited clinical efficacy and unacceptable side-effects has meant that none have entered routine clinical use. More recently several trials have suggested that the hydrophilic bile acid ursodeoxycholic acid (UDCA) is effective at slowing disease progression and is relatively free of side effects. There are, however, ongoing concerns about the ultimate efficiency of UDCA. (Jones D. E. J. et al, Hepatology, 1995, 21, 1469–73).

Whilst UDCA may be useful in slowing progression to cirrhosis, it is equally important to address the problem of symptom control. UDCA therapy appears to have little or no beneficial effect on the symptoms of PBC, with fatigue and pruritus in particular showing no response to treatment. In patients with early (stage I or II) histological disease such symptoms can be very debilitating resulting in a poor quality of life.

It has now been found that, by combining selenium, in the organic or inorganic form (eg. L-selenomethionine), β-carotene or vitamin A, ascorbic acid or a salt or ester thereof, α-tocopherol or a derivative thereof eg. vitamin E, methionine with coenzyme Q10 (ubiquinone) in a suitable formulation, a pharmaceutical composition can be prepared which alleviates the symptoms of primary biliary cirrhosis.

Such a pharmaceutical composition may be useful in preventing Systemic Inflammatory Response Syndrome (SIRS) which leads to Multiple Organ Dysfunction Syndrome (MODS). It may also be used for treating inflammatory bowel disease such as inflammatory bowel syndrome, colitis, Crohn's disease and ulcerative colitis. It may also be useful for treating mitochondrial diseases such as Huntingdon's Chorea and Leigh's disease, as well as treating fibromyalgia.

According to the invention there is provided a pharmaceutical formulation comprising organic or inorganic selenium, β-carotene and/or vitamin A, ascorbic acid or a salt or ester thereof (vitamin C), α-tocopherol or a derivative thereof, methionine and coenzyme Q10 together with a pharmaceutically acceptable carrier therefor.

The pharmaceutical formulation may comprise from 0.01 to 0.1% by weight organic or inorganic selenium, from 0.65 to 0.85% by weight β-carotene and/or vitamin A, from 32.0 to 40.0% by weight ascorbic acid or a salt or ester thereof, from 8.55 to 9.55% by weight α-tocopherol or a derivative thereof, from 53.4 to 63.4% methionine and from 5.3 to 7.5% by weight coenzyme Q10 (ubiquinone) together with a pharmaceutically acceptable carrier therefor.

Preferably the pharmaceutical formulation comprises from 0.05 mg to 0.15 mg selenium (from L-selenomethionine), from 3.0 mg to 5.0 mg β-carotene, from 150 mg to 250 mg ascorbic acid, from 40 mg to 87 mg vitamin E, from 250 mg to 600 mg methionine and from 25 mg to 50 mg coenzyme Q10, together with a suitable carrier.

According to a second aspect of the invention there is provided the use of L-selenomethionine in combination with β-carotene, ascorbic acid, D-α-tocopherylacetate, methionine and coenzyme Q10 for the preparation of a medicament for the treatment of primary biliary cirrhosis.

Such a medicament may comprise from 0,05 mg to 0.15 mg selenium (from L-selenomethionine), from 3.0 mg to 5.0 mg β-carotene, from 150 mg to 250 mg ascorbic acid, from 40 mg to 87 mg vitamin E, from 250 mg to 600 mg methionine and from 25 mg to 50 mg coenzyme Q10 in unit dosage form.

The methionine used in the present invention may be in the D or L form, or the DL racemate can be used, however, the L form is preferred. Alternatively, the methionine can be replaced by cysteine, N-acetyl cysteine or S-adenosyl methionine.

The medicament of this invention may be formulated for oral administration and therefore may be presented as plain or coated tablets, soft or hard capsules made for example from gelatin or vegetable gel, or as a sustained release formulation. Alternatively, the formulation may be in liquid form suitable for administration by ingestion, such as a syrup or elixir, or by intra-gastric administration.

In yet further alternative formulations the combination of vitamins, trace elements, sulphur-containing amino acids and coenzyme Q10 may be prepared as a suppository for rectal administration. For intravenous, intramuscular or subcutaneous administration a suitable liquid formulation can be prepared.

Excipients which may be incorporated with the active ingredients include carriers, binders, stabilizers, preservatives and flavours. Examples of suitable excipients which may be incorporated into the formulations include a binder such as gum tragacanth, acacia, corn starch, or gelatin; an excipient such as microcrystalline cellulose; a disintegrating agent such as corn starch, pregelatanized starch, alginic acid and the like; a lubricant such as stearic acid or magnesium stearate; a sweetening agent such as sucrose, lactose or saccharin, a flavouring agent such as orange, peppermint, oil of wintergreen or cherry. When the formulation is a capsule, it may contain, in addition to materials of the above type, a liquid carrier such as soya bean oil. Various other materials may be present as coatings or to otherwise modify the physical form of the formulation. For instance, tablets may be coated with shellac, sugar or both. A syrup or elixir may contain the active compound, sucrose as a sweetening agent, methyl and propyl parabens as preservatives, a dye and a flavouring such as cherry or orange flavour.

The formulation according to the invention may be administered by mouth, injection or intravenous infusion from one to six times daily, preferably three times daily.

The preferred formulation is administered by mouth and comprises a capsule, for example a soft gelatin capsule, containing the active ingredients in an oil carrier together with such additional excipients as glycerol. Soya bean oil is a suitable oil carrier, but other food grade oils such as olive oil may be used.

Use of the formulation of the present invention in the treatment of patients suffering from PBC has resulted in a significant proportion of patients reporting an improvement in symptoms, in particular the pruritus and fatigue which significantly affect quality of life.

According to yet a further aspect of the invention there is provided a method of treating diseases or disorders where an excess of free radicals may play a causative role in the aetiology of the disease, for example primary biliary cirrhosis, myocardial infarction, arthritis, cataract formation, central nervous system disorders such as Parkinson's Disease, stroke and the like, which comprises administering to a patient in need of such treatment a pharmaceutical formulation comprising organic or inorganic selenium, β-carotene or vitamin A, ascorbic acid or a salt or ester thereof, α-tocopherol or a derivative thereof, methionine and coenzyme Q10 together with a pharmaceutically acceptable carrier therefor.

The pharmaceutical formulation of the invention may also be used in the treatment of pancreatitis and fatigue syndromes.

The invention will be further described by way of reference to the following example.

EXAMPLE 1

A pharmaceutical formulation was prepared in gelatin capsule form using standard formulation techniques. Each capsule had the following composition:

Active ingredient

| | |
|---|---|
| Selenium (from L-selenomethionine) | 0.1 mg |
| β-carotene | 4.0 mg |
| Ascorbic acid | 200.0 mg |
| Vitamin E | 67.0 mg |
| L-methionine | 500.0 mg |
| Coenzyme Q10 | 34.0 mg |

In addition each capsule contained the following inactive ingredients:

Soya bean oil to make a total of 1000 mg

EXAMPLE 2

Clinical trial of formulation for the treatment of PBC

Method 24 patients (18 female, 6 male) were enroled into the trial. The mean age was 61.3±9.4 years. All patients were anti-mitochondrial antibody positive. Histological stage of the disease at last liver biopsy was as follows: Stage 1, 16 patients, Stage 2, 2 patients, Stage 3, 3 patients, Stage 4, 3 patients. 13 patients were previously taking UDCA before the start of the trial and were maintained on this therapy. 11 patients were not taking UDCA and were not started on it during the trial.

All medications patients were taking prior to the study were continued, including, where applicable, UDCA. No change in these medications was made during the study. No patient had any change in regular medication in the 3/12 before the study.

Prior to enrolment patients were clinically assessed and pruritus were assessed using a number questionnaire and a visual analogue scale. The number questionnaire invited responses for the statement "itch interferes with my sleep", and the possibilities were: every night (score 6), more than 4 nights per week (5), more than one night per week but less than 4 (4), some nights, but some weeks it won't interfere at all (3), very occasionally (2), and never (1). The visual analogue scale consisted of a line 10 cm in length, on which patients were invited to mark a response from "the worst itch possible" at 10 cm to "no itch at all" at 0 cm. Fatigue was assessed using the Fisk fatigue impact scale (19), consisting of 40 questions each of which scores from 0–4, 0 representing "no problem", 1: "small problem", 2. "moderate problem", 3; "big problem", and 4: "extreme problem".

11 patients were randomly assigned to receive the vitamin, trace elements and sulphur containing amino acids formulation alone (group 1), 13 patients were randomly assigned to receive the vitamin, trace elements and sulphur containing amino acid formulation in combination with coenzyme Q10 (group 2). No significant differences in Fisk score, itch VAS and night itch score pre-treatment were seen between the patients randomised into group 1 and group 2. There were 2 withdrawals during the 3 month trial, one patient reported increased mood swings and requested self withdrawal, and one developed a polyarthritis in her left wrist, left shoulder and right elbow, and was withdrawn by the investigators. Two blood urate levels were normal in this patient, and she responded to oral Naproxen treatment within 4 days. Both withdrawals were in the group assigned to receive the vitamin, trace elements and amino acid formulation. Compliance, as assessed by change in serum vitamin C levels pre and post therapy was 100%.

After three months of therapy the Fisk fatigue impact score and the pruritus number score and visual analogue scale were repeated, together with a further questionnaire on six symptoms; itch, tiredness, dry eyes, dry mouth, bone and joint pains, and abdominal pain. For each of the six symptoms the responses were scored "a lot worse=1", "a little worse=2", "about the same=3", "a little better=4", "a lot better=5", and "I didn't have the symptom to start with".

Results

Mean Fisk fatigue score prior to therapy was 51.8±41.9. Mean night itch score pre-therapy was 2.7±2.0. Mean itch visual analogue score (VAS) was 2.7±3.4. Excluding the patients reporting no night or day-time itch (VAS 0, night itch score 1), 13 patients reported itch by VAS (mean score 4.7±3.3) whilst 12 of the same patients reported night itch (mean score 4.3±1.7). Night itch score for the whole pre-treatment group showed a strong correlation with Fisk fatigue score prior to therapy (r=0.5, p<0.05).

Significant symptomatic improvements were observed.

i) Pruritus

A significant improvement in itch was seen in the whole group 2 both in the visual analogue scale (pre-treatment mean 2.4±3.0, post 0.4±0.7 p<0.05) and night itch score (pre-treatment mean 2.6±1.9, post mean 1.3±2.3, p<0.05); tables 1 and 2. In those patients in this group describing themselves as suffering from itch prior to treatment (VAS>0) mean VAS improved from 3.9±2.9 to 0.6±0.8 (p=0.001); FIG. 1. In those describing night itch prior to treatment the mean score improved from 4.3±1.4 to 1.7±0.8 (p<0.005). On direct questioning 6/8 patients in this group reporting itch pre-treatment said that it had improved with therapy whilst 2/8 reported no improvement. No statistically significant improvement was seen in itch assessed either in terms of VAS or night itch score in group 1, although 3/5 patients reporting itch on direct questioning suggested that it had improved (2/5 reporting no change).

ii) Fatigue

The Fisk fatigue impact score was reduced in 16 of the 22 (72%) patients who completed the 3 months of trial medication (group 1: 6/9 (67%); group 2 10/13 (72%); FIG. 2. 14/22 (64%) patients reported that their fatigue was "a lot better" on direct questioning. A significant correlation was seen between the ratio of the Fisk score pre- and post-treatment and reported symptomatic change score (r=0.44, p<0.05). The symptomatic improvement was more marked in group 2 (mean 20 point reduction out of 160 point score) than group 1 (mean 4.5 point reduction out of 160 point score). Due to the high standard deviations, these reductions were not significant (table 3). In the symptoms questionnaire 14/22 patients reported tiredness improvement (5/9 group 1, 9/13 group 2); FIG. 1.

iii) Other Symptoms

9/22 subjects reported dry eyes improvement (9/14 patients reporting this symptom). Improvement was seen in 3/9 (3/5) patients in group 1 and 6/13 (6/9) patients in group 2. 5/22 (5/12) subjects reported dry mouth improvement (group 1 2/9 (2/4), group 2 2/13 (218)). 3/22 (3/9) subjects reported abdominal pain improvement (group 1 2/9 (2/6), group 2 1/13 (1/3)). 4/22 (4/13) subjects reported bone and joint pain improvement (group 11/9 (115), group 2 3/13 (3/8)).

TABLE 1

Itch Visual Analogue Scale
(decrease indicates therapeutic benefit)

|  | Before treatment | After treatment | t-test |
|---|---|---|---|
| Group 1 | 3.3 ± 4.2 | 2.5 ± 3.2 | p = ns |
| Group 2 | 2.4 ± 3.0 | 0.4 ± 0.7 | p < 0.05 |

TABLE 2

Night Itch

|  | Before treatment | After treatment | t-test |
|---|---|---|---|
| Group 1 | 3.0 ± 2.3 | 1.9 ± 1.6 | p = ns |
| Group 2 | 2.6 ± 1.9 | 1.3 ± 0.7 | p < 0.05 |

TABLE 3

Fisk fatigue impact score (score out of 160,
reduction indicates therapeutic benefit)

|  | Before treatment | After treatment | t-test |
|---|---|---|---|
| Group 1 | 43.7 ± 32.5 | 39.2 ± 40.6 | p = ns |
| Group 2 | 60.3 ± 49.3 | 40.3 ± 37.5 | p = ns |

What is claimed is:

1. A pharmaceutical formulation for treating liver disorders selected from the group consisting of primary biliary cirrhosis, viral hepatitis, steatohepatitis and alcoholic cirrhosis comprising 0.01% by weight L-selenomethionine, 0.65% by weight β-carotene and/or vitamin A, 32.0% by weight ascorbic acid or a salt or ester thereof, 8.55% by weight α-tocopherol, vitamin E or D-α-tocopheryl acetate, 53.4% by weight methionine and 5.3% by weight coenzyme Q10 together with a pharmaceutically acceptable carrier thereof.

2. The formulation according to claim 1, wherein the methionine is L-methionine.

3. A pharmaceutical formulation for treating liver disorders selected from the group consisting of primary biliary cirrhosis, viral hepatitis, steatohepatitis and alcoholic cirrhosis comprising from 0.05 mg to 0.15 mg L-selenomethionine, from 3.0 mg to 5.0 mg β-carotene, from 150 mg to 250 mg ascorbic acid, from 40 mg to 87 mg vitamin E, from 250 mg to 600 mg methionine and from 25 mg to 50 mg coenzyme Q10 together with a pharmaceutically acceptable carrier therefor.

4. The formulation according to claim 3, wherein the methionine is L-methionine.

5. A method of treating liver disorders selected from the group comprising consisting of primary biliary cirrhosis, viral hepatitis, steatohepatitis, and alcoholic cirrhosis comprising administering to a patient in need thereof a pharmaceutical composition comprising
   0.01% by weight L-selenomethionine;
   0.65% by weight β-carotene and/or vitamin A;
   32.0% by weight ascorbic acid or a salt or ester thereof;
   8.55% by weight α-tocopherol, vitamin E or D-α-tocopheryl acetate;
   53.4% by weight methionine; and
   5.3% by weight coenzyme Q10 based on the total weight of the formulation; and
   a pharmaceutically acceptable carrier therefor.

6. The method of claim 5, wherein the methionine is L-methionine.

7. A method of treating liver disorders selected from the group consisting of primary biliary cirrhosis, viral hepatitis, steatohepatitis, and alcoholic cirrhosis comprising administering to a patient in need thereof a pharmaceutical composition comprising 0.05 mg to 0.15 mg L-selenomethionine, from 3.0 mg to 5.0 mg β-carotene, from 150 mg to 250 mg ascorbic acid, from 40 mg to 87 mg vitamin E, from 250 mg to 600 mg methionine and from 25 mg to 50 mg coenzyme Q10 together with a pharmaceutically acceptable carrier therefor.

8. The method of claim 7, wherein the methionine is L-methionine.

* * * * *